United States Patent [19]

Fliegel

[11] 4,176,349
[45] Nov. 27, 1979

[54] INTRAVENOUS ALARM SYSTEM

[76] Inventor: Martin S. Fliegel, 8213 Oakdale Ave., Canoga Park, Calif. 91306

[21] Appl. No.: 857,291

[22] Filed: Dec. 5, 1977

[51] Int. Cl.$^2$ ............................................. G08B 21/00
[52] U.S. Cl. ................................. 340/613; 128/214 E; 177/48; 200/85 R
[58] Field of Search ............... 340/606, 613, 620, 624, 340/688; 177/48; 200/85 R; 128/214 E, DIG. 13

[56] References Cited

U.S. PATENT DOCUMENTS

| 450,923 | 4/1891 | Woolley | 200/85 R X |
| 513,829 | 1/1894 | Schureman | 340/688 X |
| 2,706,755 | 4/1955 | Krasno | 340/613 X |
| 2,744,177 | 5/1956 | Barber | 34/624 X |
| 3,389,387 | 6/1968 | Hulse et al. | 340/613 X |
| 3,390,238 | 6/1968 | O'Neill | 200/85 R |
| 3,425,415 | 2/1969 | Gordon et al. | 340/613 X |
| 3,656,138 | 4/1972 | Hamma | 177/48 |

FOREIGN PATENT DOCUMENTS 1119883  6/1956  France .................... 200/85 R

Primary Examiner—John W. Caldwell, Sr.
Assistant Examiner—Daniel Myer

[57] ABSTRACT

A monitoring device which monitors the extent of infusion of intravenous solutions and provides an alarm signal when such infusion has progressed to a predetermined degree. The device comprises a cylindrical container to which is coupled, at its upper end, an attaching member for suspending the device from an intravenous solution supporting stand. Peripherally disposed about the cylindrical container are electrical sockets adapted such that each socket may accept an associated electrical plug. Extending through and below the lower end of the cylindrical container is a suspension member having a hook section for suspending an intravenous solution container. A helical spring is disposed within the cylindrical container, coaxially surrounding that portion of the suspension member which extends into the cylindrical container. The vertical position of the spring is defined by the lower internal end of the cylindrical container and by the upper extremity of the suspension member disposed within the container. At the juncture of the upper extremity of both the suspension member and helical spring is an actuator adapted such that electrical contact may be selectively made between the actuator and the electrical plug. The helical spring, suspension member, electrical plug, and actuator are disposed within the container such that as the quantity of intravenous solution diminishes, the actuator moves vertically upward toward the plug, ultimately making electrical contact and thereby actuating an alarm.

9 Claims, 3 Drawing Figures

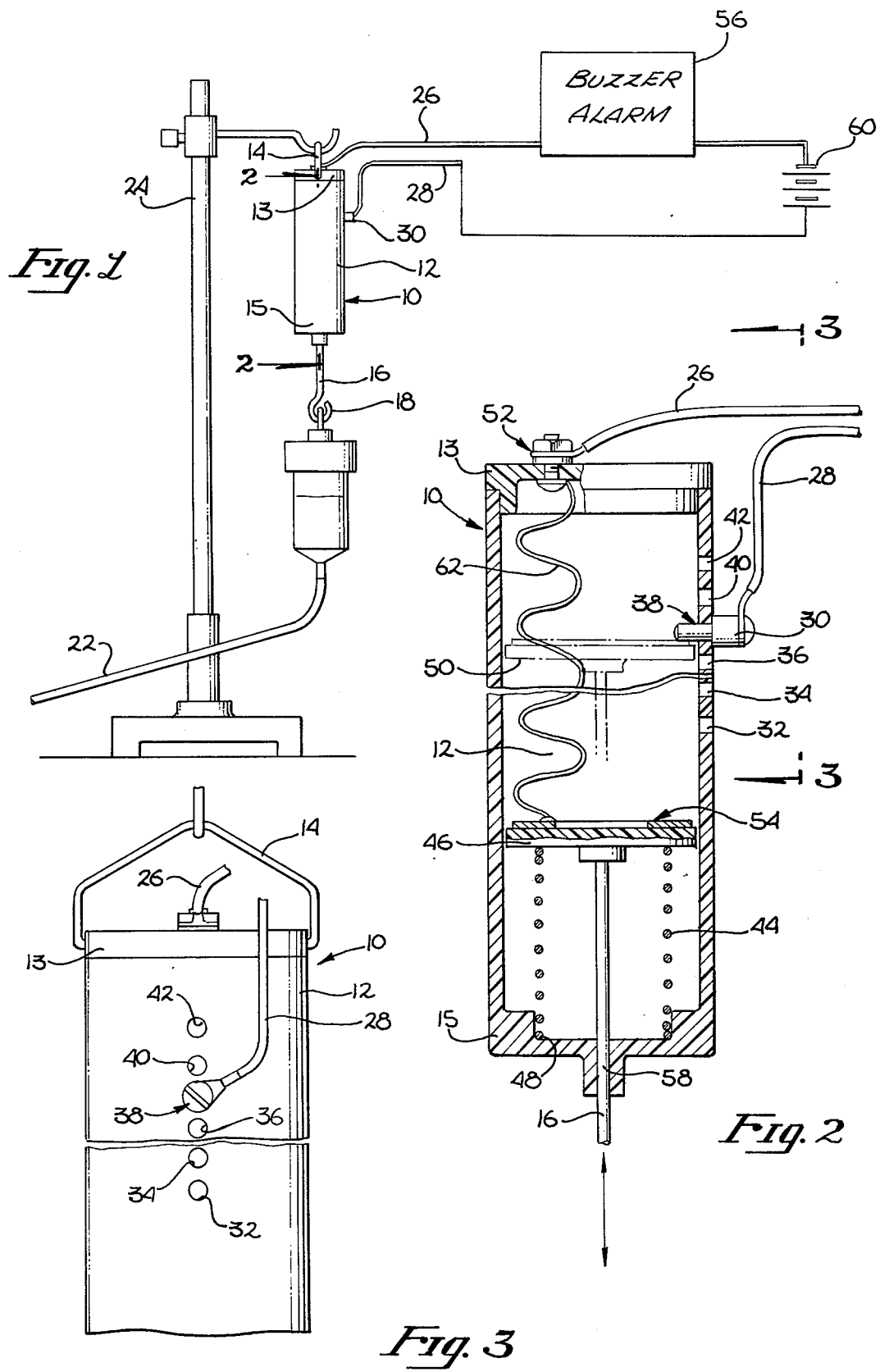

INTRAVENOUS ALARM SYSTEM

BACKGROUND OF THE INVENTION

1. Field of the Invention

The present invention relates to the field of infusion monitoring and alarm devices, and more specifically, a portable, yet accurate alarm monitor.

2. Prior Art

One important and frequently utilized medical procedure is the intravenous infusion of a variety of fluids, such as whole blood, plasma, dextrose, physiologic saline, and other medication. However, several problems are associated with this procedure. One difficulty is that of accurately administering some portion of a standard unit of such fluids; that is, with the typical intravenous injection system it is difficult to terminate the infusion, after some predetermined quantity of fluid has been administered, without frequent, time consuming, observations of the quantity of remaining solution. This requires frequent checking of the fluid level by trained personnel, such as a nurse. Another problem associated with intravenous infusion is that the complete injection of one unit of fluid may be accomplished without notification of the attending personnel. Thus, when continuous administration is required, completion of one stage of such administration may go unnoticed, resulting in some period of time before it becomes known that all the fluid has been infused into the patient. Beyond this undesirable lapse in time, the termination of the injection may result in clotting and occlusion of the needle, which has been supplying the intravenous solution, due to backflow of the patient's blood into the needle; this would necessitate removal, location of another vein, and another insertion. Accordingly, is has been necessary that constant attention be given to the patient when receiving an infusion.

What is required to solve the problems noted above is an infusion monitoring device which will provide a warning signal when the infusion has progressed to some predetermined extent such that when it is desired to administer only a portion of a standard unit of solution, the monitoring device may be adjusted such that an alarm will be given prior to or at the exact completion of the desired infusion. When it is desirous to administer a complete unit of liquid, the device should be adjustable such that an alarm will be given prior to the complete infusion of one standard unit of such liquid or solution; a new supply of fluid may then be provided without breaking the continuity.

However, beyond this signaling capability, a monitoring device should also have an initial and a long-term accuracy so that over its useful life it may be used with confidence. If initially or after a long period of use, this sensing is not performed accurately, when it is being used to signal that the desired amount of solution has been infused, inaccurate administration will result—either too little or too much intravenous solution will have been infused. If too little fluid has been infused, only inconvenience to attending personnel will result, but if too much fluid has been administered, the patient may suffer adverse consequences. And, when the device is being used to signal that the infusion of one unit of solution is near completion, the alarm will be given either prematurely, again resulting in wasted effort by those notified by the alarm, or after the complete infusion of one unit, resulting in possible clotting and occlusion of the needle. Manifestly, if such initial and long-term accuracy is not maintained, the problems of infusion noted above will be aggravated and ultimately the use of the device will be severely diminished. Finally, to provide maximum useful life, and consequently minimum expense, the monitoring device should be simply constructed, utilizing direct and effective design principles, and should be easily portable.

Devices which monitor the infusion of intravenous solutions and provide a warning when such infusion has reached a predetermined extent are well known in the art. These devices usually utilize some form of spring extension which provides, in effect, a weighing of the slowly decreasing supply of fluid. In these devices a switch means is provided which acutates a warning signal when the weight of the fluid being administered has reached the desired level. While these devices may have initially provided accurate signaling capability, their inherent design principle of weight sensing by spring extension has failed to provide the requisite long-term accuracy. This failure is due to the ever-increasing fatigue of the spring caused by its repeated extension. Over a period of time this fatigue results in a change in the spring constant; that is, the reaction of the spring to a given force varies as the degree of fatigue increases. Thus, as these devices are used, the setting which initially provided a signal at the desired fluid level no longer provides a signal at that level. Moreover, many of these devices are relatively complex and are therefore expensive.

One prior art attempt to provide the capabilities noted above is described by O'Neill, U.S. Pat. No. 3,390,238. O'Neill utilizes an extension spring-biased member having a hook portion for supporting an intravenous container. Associated with the spring-biased member is an arm which, upon the contents of the container reaching a predetermined level, is adapted to make an electrical contact so as to actuate an alarm system. Another prior art monitoring device is disclosed by Hulse et al, U.S. Pat. No., 3,389,387. Hulse also utilizes an extension spring-biased member which supports an intravenous container by a hook portion. Associated with the spring-biased member is an actuator, adapted to actuate a conventional microswitch when the intravenous container weight, and thus the fluid level, has reached a predetermined level. In both the O'Neill and Hulse devices, the problem of long-term accuracy was not effectively solved as their device's level adjustment repeatability will shift with usage due to spring fatigue. Further, these prior art devices fail to meet the previously discussed requirements of simplicity and inexpensiveness.

In the present invention the problem of long-term accuracy is solved by utilizing a simple but effective weighing system whose principle design feature is that of spring compression, not spring extension. This feature greatly minimizes spring fatigue, thus minimizing spring constant shift and consequently providing long-term accuracy of level threshold. Moreover, the present invention provides a device which is both inexpensive and uncomplicated to produce, and utilizes an electrical plug system which permits various quantities of fluid to be administered without complex adjustment of the device.

BRIEF SUMMARY OF THE INVENTION

The present invention is a device which accurately monitors the process of intravenous infusion and provides an alarm signal when such infusion has reached some predetermined extent. The monitoring device comprises a tubular container which may be suspended from a typical intravenous infusion stand by an attaching member which is coupled to the upper portion of the container. Disposed within and extending through and below the tubular container is a suspension member. At the lower extremity of this member is a hook section adapted to suspend the intravenous solution container whose level of solution is to be monitored. That portion of the suspension member within the tubular container is coaxially disposed within a helical spring. The vertical position of the spring is defined by the lower end of the container and by the upper extremity of the suspension member. At the juncture of both the upper extremity of the helical spring and suspension member is an actuator, to which is attached an electrical wire which extends through and beyond the upper end of the tubular container. The actuator is adapted such that it may make electrical contact with an electrical plug located in one of several associated sockets disposed peripherally about the container. Attached to the plug is another electrical wire which, in conjunction with the wire leading from the actuator, forms electrical signaling wires.

The suspension member, helical spring, actuator, and electrical plug are configured such that when a container of intravenous solution is initially suspended from the hook section of the suspension member the helical spring is compressed such that the actuator is disposed some distance below the plug. Due to the upward force of the compressed spring, the actuator will move vertically toward the electrical plug as the fluid within the suspended container is depleted. When the intravenous solution has been administered to some predetermined extent, the actuator will have moved upward such that it will make physical and electrical contact with the plug. This electrical contact will provide an alarm or alarm signal signifying that the infusion has progressed to the desired extent.

Versatility is created in the monitoring device by providing the warning capability noted above for a variety of sizes, shapes and weights of intravenous infusion containers. By placing the electrical plug in the socket which corresponds to the weight of the container to be monitored, the alarm will be activated when the solution remaining in that container has reached some predetermined level. Thus, the device is configured such that the plug would be placed in an upper socket when a relatively lighter container is to be monitored and conversely, it would be placed in a lower socket when a relatively heavier container is to be monitored.

Both initial and long-term monitoring accuracy is provided by the present invention through its utilization of spring compression design and low frictional guiding surfaces. Through the use of helical spring compression instead of spring expansion and the proper selection of a spring constant for the helical spring, spring fatigue has been minimized, resulting in long-term maintenance of the initial spring constant. This spring constant consistency results, in turn, in long-term accuracy so that the alarm signal will be consistently activated at a consistent level of remaining solution. In addition, the suspension member is accurately positioned and guided by a low friction aligning means which further contributes to both the initial and long-term monitoring accuracy.

The novel features which are believed to be characteristic of the invention, both as to its organization and method of operation, together with further objectives and advantages thereof will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

BRIEF DESCRIPTION OF THE DRAWINGS

FIG. 1 is a perspective view of the monitoring device suspended from a typical intravenous solution supporting stand and suspending, in turn, a container of the type typically used to hold infusion solutions.

FIG. 2 is a vertical cross-sectional view taken on substantially the line 1—1 of FIG. 1.

FIG. 3 is an enlarged side elevational view of the monitoring device of FIG. 1, as seen from the line 3—3 of FIG. 2.

DETAILED DESCRIPTION OF THE INVENTION

Referring first to FIGS. 1 and 2, monitoring device 10 is shown suspended by its attaching member 14 from a typical intravenous infusion stand 24. In this configuration the device monitors the amount of intravenous solution remaining in dispensing container 20 and provides an alarm signal to buzzer alarm 36, with its associated electrical power source 60, when the amount of solution reaches some predetermined level. In the presently preferred embodiment, the monitoring device container 12 is a generally tubular configuration having a top member 13 and a bottom member 15, however, it is within the scope of the invention to use other configurations. In the presently preferred embodiment, the top member 13 is removeable from the container 12. This permits entry into the container to change the spring and the like. On the other hand, the bottom member 15 is discretely molded so as to be a continuation of the container 12.

Extending through bottom member 15 and below the tubular container 12 is a suspension member 16 having a hook section 18 which is adapted to suspend a typical intravenous solution container 20. Such hooks are well known in the art. The suspension member 16 and more specifically, the hook 18 is slideably positioned in the container 12 by an alligning member 58. Alligning member 58 is a generally tubular protrusion extending downward from the container 12 with an opening disposed therethrough. Member 58 accurately positions suspension member 16 therein. This further improves the longevity and accuracy of the device of this invention. Leading from container 20 to the patient is a typical intravenous tube 22.

Also coupled to the container 12 is electrical plug 30 extending from the outer wall of the container. Attached to both electrical plug 30 and top member 13 of container 12 are electrical signaling wires, 28 and 26 respectively. These wires are joined to a power source such as battery 60 and to buzzer alarm 56. Alarm 56 is any of the well known electrical alarm devices and will not be discussed further herein.

Now referring to FIG. 2, it can be seen that within tubular container 12 a generally flat circular actuator 46 is attached at the upper extremity of suspension member 16. Although in the presently preferred embodiment the actuator 46 is generally flat and circular, it is within the scope of the invention to use other configurations. Electrical feedthrough 52 connects signaling wire 26 with the electrically conductive surface 54 on actuator 46 by means of flexible conductive wire 62. Electrical feedthrough 52 in the presently preferred embodiment is a bolt and associated nut. Wire 26 is joined to the top member 13 via the nut, and wire 62 is also joined to the top member 13 via the bolt such that wires 26 and 62 are electrically coupled together.

Coaxically surrounding member 16 is a helical spring 44. This spring is vertically positioned at its lower end by groove 48 and at its upper end by the juncture of the spring 44 with the lower surface of actuator 46. It is the unique positioning of helical spring 44 which represents one point of novelty and a destinct improvement over the prior art. Because of the positioning of spring 44, the problem of poor accuracy and long life associated with prior art devices is substantially improved.

Also illustrated in FIG. 2 is electrical plug 30 which is shown inserted in an associated socket 38. Electrical plug 30 is of a type as is well known in the art. In the presently preferred embodiment, plug 30 is arranged and configured so as to extend through socket 38 and into the container 12 a predetermined distance. Attached to the electrical plug is signaling wire 28. Located above and below socket 38 are other sockets, 32, 34, 36, 40 and 42, which sockets can correspond to different volume of containers (500 cc glass, 1000 cc glass or 500 cc plastic bag, etc. for example), different alarm times as more fully described herein.

By references to FIGS. 1 and 2 it may be understood that intravenous solution container 20 exerts a downward force on member 16; this force is proportional to the weight of the solution within the container and thus to the volume of the solution remaining in the container. Because actuator 46 is attached to member 16, the force exerted by the container tends to pull the actuator 46 downward. Opposing this movement is the tendency of the compressed helical spring 44 to expand to its normal position. Thus, when a container of intravenous solution 20 is initially suspended from the monitoring device, actuator 46 and spring 44 are configured such that the actuator is located in some position in the lower extremity of tubular container 12. As the intravenous fluid is administered, the weight of container 20 decreases so that the helical spring moves the actuator upward in tubular container 12. When the fluid remaining in container 20 has reached a specific level, the actuator 54 will have moved upward to some position 50 (shown by dashed lines in FIG. 2) such that the electrically conductive surface 54 makes physical and electrical contact with electrical plug 30, thereby activating buzzer alarm 56 due to the electrical coupling of wires 26 and 28.

By reference to FIGS. 2 and 3 it may be seen that the monitoring device may be adjusted to provide an alarm signal for a variety of different sizes, shapes, and weights of intravenous solution containers by placing electrical plug 30 in one of several of the associated sockets, 32, 34, 36, 38, 40, 42. The electrical sockets 32–42 may be labeled to indicate which size of container corresponds to a particular socket. The device is so configured that sockets corresponding to relatively heavier containers are located below those sockets which correspond to relatively lighter containers. Thus, by placing plug 30 in the socket 32–42 which corresponds to the size of container to be monitored, the alarm will be activated when the solution remaining in that container has reached some minimum level.

Because the relationship of the location of the actuator 46 and the weight of the remaining solution in container 20 determines when the alarm is actuated, it is important that this relationship remain essentially constant throughout the use of the device to provide long-term accuracy. This constant relationship is achieved in the present invention through the use of novel design principles; first, the stress on helical spring 44 is minimized by utilizing a spring compression principle. Secondly, initial as well as long-term accuracy is promoted by the utilization of aligning member 58. This member provides axial alignment of suspension member 16 by selectively constraining member 16 to a precisely defined vertical path. By using low friction construction, alignment member 58 ensures that the vertical force exerted by spring 44, and any horizontal force exerted by container 20, are translated into precise vertical movement within tubular container 12. Thus, with the combined effect of compression spring design and low friction alignment methods, a similar positioning of electrical plug 30 will consistently give an alarm at the predetermined level of solution remaining in container 20.

There has been described herein a new and novel infusion monitoring device which accurately provides an alarm when an intravenous infusion has progressed to a predetermined extent. While one specific embodiment of the present invention has been disclosed and described in detail, herein, it will be understood by those skilled in the art that various changes in form and detail may be made therein without departing form the spirit and scope of the invention.

I claim:

1. A monitoring apparatus comprising:
(a) a container having a top member and a bottom member;
(b) an attaching member for attaching said container to an associated support such that said container extends downward thereform in a generally vertical configuration, said attaching member coupled to said container adjacent said top member;
(c) a plurality of electrical sockets disposed through said container, each said socket adapted to accept an associated electrical plug;
(d) an elongated suspension member slideably disposed in said container adjacent to and extending through said bottom member, said suspension member having:
  (i) a shaped section arranged and configured to selectively engage a dispensing container, said shaped section disposed on said suspension member adjacent the bottom thereof, and
  (ii) an actuator disposed on said suspension member adjacent the top thereof and having an electrically conductive surface, said surface arranged and configured to selectively engage said electrical plug;
(e) a helical spring disposed in said container, circumferically disposed about said suspension member so as to be journalled between said actuator and said bottom of said container; and
(f) an alarm circuit system, said alarm system having an alarm device electrically coupled to said electrical plug, said electrical plug arranged and configured to be selectively disposed in one of said sockets and extend through said container so as to limit the upward movement of said suspension member by selectively engaging said conductive surface on said actuator, said alarm system further being electrically coupled to said conductive surface on said actuator whereby when said suspension member and said actuator are disposed downward, said helical spring is compressed and said actuator disengages said electrical plug thereby deactivating said circuit, and when said suspension member slideably travels upward toward said top member of said container, said upward movement is stopped upon engagement of said conductive surface with said electrical plug thereby activating said alarm device.

2. Apparatus according to claim 1, wherein the location of each of said electrical sockets corresponds to an associated dispensing container having a predetermined weight.

3. Apparatus according to claim 2, wherein said plurality of electrical sockets are each marked so as to denote size of said associated dispensing container.

4. Apparatus according to claim 3, wherein said suspension member is laterally positioned and guided through said bottom member of said container by an aligning means.

5. Apparatus according to claim 4, wherein said electrically conductive surface on said actuator is electrically coupled to said alarm system by a flexible electrically conductive wire, said wire arranged and configured to couple said surface on said actuator with an electrical feedthrough device, said feedthrough device disposed adjacent to and extending through said top member of said container, said feedthrough device further being electrically coupled to said alarm system.

6. Apparatus according to claim 5 wherein said alarm system comprises a buzzer device and an electrical power means, whereby said buzzer device and said electrical power means are electrically coupled so as to provide an alarm upon engagement of said actuator with said electrical plug.

7. A monitoring apparatus comprising:
(a) a tubular container having a top member and a bottom member;
(b) an attaching member for attaching said container to an associated support such that said container extends downward therefrom in a generally vertical configuration, said attaching member coupled to said container adjacent said top member;
(c) a plurality of electrical sockets disposed through said tubular container, each said socket adapted to accept an associated electrical plug;
(d) a rod member slideably disposed in said tubular container adjacent to and extending through said bottom member, said rod member having:
 (i) a hook section arranged and configured to selectively engage a dispensing container, said hook section disposed on said rod member adjacent the bottom thereof, and
 (ii) a generally flat circular actuator disposed on said rod member adjacent the top thereof, said actuator being electrically conductive, and arranged and configured to selectively engage said electrical plug;
(e) a helical spring disposed in said tubular container, circumferially disposed about said rod member so as to be journalled between said circular actuator and said bottom of said container; and
(f) an alarm circuit system, said alarm system having an alarm device electrically coupled to said electrical plug, said electrical plug arranged and configured to be selectively disposed in one of said sockets and extend through said tubular container so as to limit the upward movement of said rod member by selectively engaging said circular actuator, said alarm system further being electrically coupled to said actuator whereby when said rod member and said actuator are disposed downward, said helical spring is compressed and said actuator disengages said electrical plug thereby deactivating said circuit, and when said rod member slideably travels upward toward said top member of said tubular container said upward movement is stopped upon engagement of said conductive surface with said electrical plug thereby activating said alarm device.

8. Apparatus according to claim 7, wherein said suspension member is laterally positioned and guided through said bottom member of said container by an aligning means.

9. Apparatus according to claim 7, wherein said electrically conductive surface on said actuator is electrically coupled to said alarm system by a flexible electrically conductive wire, said wire arranged and configured to couple said surface on said actuator with an electrical feedthrough device, said feedthrough device disposed adjacent to and extending through said top member of said container, said feedthrough device further being electrically coupled to said alarm system.

* * * * *